(12) United States Patent
Lubys

(10) Patent No.: US 9,982,268 B2
(45) Date of Patent: May 29, 2018

(54) VECTORS FOR CLONING

(75) Inventor: Arvydas Lubys, Vilnius (LT)

(73) Assignee: Thermo Fisher Scientific Baltics UAB, Vilnius (LT)

(*) Notice: Subject to any disclaimer, the term of this patent is extended or adjusted under 35 U.S.C. 154(b) by 1520 days.

(21) Appl. No.: 12/167,527

(22) Filed: Jul. 3, 2008

(65) Prior Publication Data

US 2009/0042249 A1  Feb. 12, 2009

(30) Foreign Application Priority Data

Jul. 6, 2007 (GB) .................................. 0713179.0

(51) Int. Cl.
*C12N 15/64* (2006.01)
*C12N 15/65* (2006.01)

(52) U.S. Cl.
CPC ............. *C12N 15/64* (2013.01); *C12N 15/65* (2013.01)

(58) Field of Classification Search
CPC ................................ C12N 15/64; C12N 15/65
See application file for complete search history.

(56) References Cited

FOREIGN PATENT DOCUMENTS

WO  WO 98/38205 A1  9/1998
WO  WO 2004/106526 A1  12/2004

OTHER PUBLICATIONS http://www.fermentas.com/en/support/technical-reference/phage-plasmid-dna/pjet12, 2012.*
Genbank accession No. EF694056.1, 2007.*
Heyman et al., 1999, Genome Research vol. 9, 383-392.
Liu et al., 1998, Current Biology, vol. 8, 1300-1309.
Sadowski, 2003, BMC Biotechnology, 3:9, 1-10.
Hartley et al., 2000, Genome Res 10: 1788-1795.
Bolivar et al., Gene 1977, 2:95-113.
Vieira, J., Messing, J., 1982, Gene, 19: 259-268.
Messing et al., 1977, Proc. Natl. Acad. Sci. USA 74:3642-3646.
Messing et al., 1981, Nucl. Acids Res. 9:309-321.
Young-Jun et al., Critical Reviews in Biotechnology, 22, 225-244, 2002.
Dente, L., Cesareni, G., Cortese, R., Nucleic Acids Res., 1983, 11, 1645-1655.
Macrina FL. et al. Gene. 1982; 19:345-53.
Mongkolsuk S. et al. Gene. 1994; 143:145-6.
Studier and Moffatt J., Mol Biol. 1986; 189:113-30.
Alting-Mees MA, and Short JM., Nucleic Acids Res. 1989; 17:9494.
Mead, D.A., Szczesna-Skorupa, E., Kemper, B. Protein Eng. 1986 1: 67-74.
Close TJ et al. Gene. 1983; 23:131-136.
Saida F et al., Biotechnol Prog. May Jun. 2003;19(3):727-33.
Yazynin S et al., FEBS Lett. Jun. 11, 1999;452(3):351-4.
Schlieper D et al., Anal Biochem. Mar. 15, 1998;257(2):203.
Henrich and Schmidtberger, Gene. Feb. 27, 1995;154(1):51-4.
Lutz and Bujard, Nucleic Acids Res. Mar. 15, 1997;25(6):1203-10.
Trudel P et al. Biotechniques. 1996; 20:684-93.
Yazynin SA et al. Gene. 1996; 169:131-132.
Manoil and Bailey, J. Mol. Biol., 1997, 267, 250-263.
Biondi et al., Nucleic Acids Res., 26, 4946-4952.
Savilahti et al., EMBO Journal, 14(19), 4893-4903, 1995.
Janulaitis et al., FEBS Lett., 161 (1983) 213-216.
Chang and Cohen, J.Bacteriol. 134: 1141-1156, 1978.
Allet, B. 1979, Cell 16:123-129.
Mann, M.B., Rao,R.N. and Smith,H.O. (1978) Gene, 3, 97-112.
Whitehead, P.R. and Brown,N.L. (1985) Arch. Microbiol., 141, 70-74.
Stankevicius et al., Gene 157, (1995) 49-53.
Lubys et at., NAR, 1996, 24(4), 2760-2766 p.
JET1 product information, Molecular Cloning, Fermentas, 5 pages.
Kim et al., Biotechnology Letters, 26, 1659-1663, 2004.
Manoil and Traxler, Methods, 2000, 20(1a), 55-61.
European Search Report dated Sep. 10, 2008 (five (5) pages).
Jean-Michel Betton, "Cloning Vectors for Expression—PCR Products", BioTechniques, Sep. 2004, pp. 346-347, vol. 37, No. 3.
Delbert et al., "Crystal structure of MunI restriction endonuclease in complex with cognate DNA at 1.7 Å resolution", The EMBO Journal, vol. 18, No. 21, pp. 5805-5816, 1999.

* cited by examiner

*Primary Examiner* — Addison D Ault
(74) *Attorney, Agent, or Firm* — Crowell & Moring LLP

(57) ABSTRACT

A vector for transformation into a host cell is described comprising a toxic gene encoding a product that is lethal to the host cell, wherein the toxic gene comprises:
  an essential sequence region whose integrity is necessary in order for the encoded toxic gene product to be lethal to the host cell;
  an inessential sequence region whose integrity is not essential in order for the encoded toxic gene product to be lethal to the host cell;
  a regulatory sequence inserted in-frame into the inessential sequence region; and
  a cloning site within the essential sequence region for insertion of a nucleic acid sequence,
wherein the regulatory sequence and the cloning site are positioned so as to allow the regulatory sequence to be operably linked to a nucleic acid sequence when the nucleic acid sequence is inserted into the cloning site.

12 Claims, 10 Drawing Sheets

FIGURE 7

Figure 1:
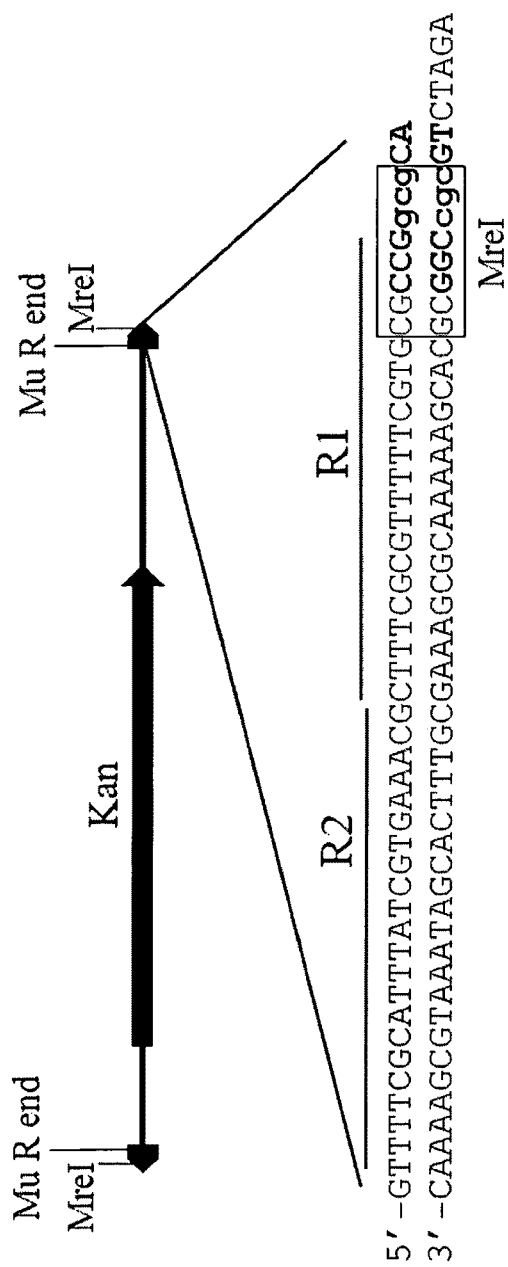

1-HA 5'-ACTAGTAAGGAGATAAGAATGCTGAATAATCCTAAATACCCTAAAG-3'
2-HA 5'-GCGGCCGCTTATCTATTTTCCACTAAAAACA-3'

VECTORS FOR CLONING

The present invention relates to new vectors for the cloning of nucleic acid molecules, especially positive selection vectors. The invention also relates to kits for cloning and processes for using the vectors of the present invention.

Genetic engineering describes a large range of activities extending from the manipulation of DNA to the introduction of new or altered DNA molecules into cells of eukaryotes or microorganisms resulting in altered genome content of the transformed host. Despite the variety of purposes of genetic engineering, the same intermediate step, cloning of a DNA sequence of interest, is always carried out. Cloning describes insertion of a DNA sequence of interest into a cloning vector which is capable of replication, and its propagation by means of recombinant molecule replication within the host cell. There are many types of cloning vectors including plasmids, bacteriophages, bacterial artificial chromosomes and yeast artificial chromosomes. However, plasmids are perhaps most commonly used for this purpose.

Numerous plasmid vectors are available for cloning of DNA fragments in *Escherichia coli* cells. In general, plasmid cloning vectors are relatively small double-stranded circular DNA molecules, which contain a replication region responsible for autonomous replication, an antibiotic resistance gene which ensures selection of transformed cells using growth media supplemented with the corresponding antibiotic, and at least one cloning site.

There are three enzyme-mediated approaches to DNA fragment insertion into the cloning vector. Topoisomerase I-mediated cloning technology uses properties of Vaccinia DNA topoisomerase I (Heyman et al., 1999, Genome Research Vol 9, 383-392). Recombinase-based cloning technologies exploit the properties of bacterial or viral site-specific recombinases, like the bacteriophage P1 Cre, the *Saccharomyces cerevisiae* FLP or the bacteriophage lambda integrase (Liu et al., 1998, Current Biology, Vol 8, 1300-1309; Sadowski, 2003, BMC Biotechnology, 3:9, 1-10; Hartley et al, 2000, Genome Res 10: 1788-1795). However, to date the most popular approach is T4 DNA ligase-mediated ligation between a vector and a DNA fragment of interest. T4 DNA ligase catalyzes the formation of a phosphodiester linkage between a 5'-phosphoryl group and an adjacent 3'-hydroxyl group of duplex DNA in a blunt-ended or cohesive-ended configuration. In the presence of a linear cloning vector molecule and a DNA fragment of interest the ligation reaction produces not only desired hybrid molecules, but also a large fraction of self-ligated circular molecules. Self-ligated vector molecules result in a background, making identification of required recombinant molecules quite complicated. To overcome this problem, the step of treating the linearised cloning vectors with phosphatase prior to ligation has been introduced into cloning practice. Phosphatase removes 5'-phosphates from both ends of linear vector molecules, making self-ligation impossible. This improvement reduces the background significantly. However, the method does not allow direct identification of those transformants harbouring recombinant plasmids for further analysis.

Two major strategies, namely insertional inactivation and positive selection, have been developed and implemented in order to deal with the problem of identifying transformants containing recombinant plasmids.

The approach of insertional inactivation uses genes that are not toxic to the host and confer easily detectable phenotypic feature. If such a gene, located within the cloning vector, is destroyed by an inserted foreign DNA fragment, the resulting loss of function allows the differentiation of recombinants from empty vector molecules.

Cloning vector pBR322 (Bolivar et al., Gene 1977, 2:95-113) and plasmids of pUC series (Vieira, J., Messing, J., 1982, Gene, 19: 259-268) are typical examples of such cloning vectors, which exploit the technique of insertional inactivation. The vector pBR322 contains separate genes conferring resistance to ampicillin (gene bla) and to tetracycline (gene tet). There are several unique restriction endonuclease sites within the tet gene, and insertion of foreign DNA fragment into any of these sites results in inactivation of the tet gene. Host cells carrying recombinant plasmids will become tetracycline-sensitive and ampicillin-resistant, whereas self-ligated vector molecules will confer resistance to both antibiotics to the host cells carrying them. Thus, required clones can be identified by the growing of transformants on ampicillin-containing plates and then replicating resulting transformants onto ampicillin-containing plates either supplemented with tetracycline or not. Those colonies which survive on the ampicillin but not on ampicillin-tetracycline containing plates are likely candidates for further analysis.

Plasmids of pUC series are other cloning vectors of this type which utilise the technique of insertional inactivation. In addition to the replication region and to the gene bla which confers resistance to ampicillin, these plasmids harbour a short fragment of *Escherichia coli* lac operon which contains the lac promoter and a 5'-terminal part of the lacZ gene encoding the N-terminal fragment of beta-galactosidase (N-LacZ). This fragment, whose synthesis can be induced by an inducer of lac operon, isopropyl beta-D-thiogalactopyranoside (IPTG), is capable of intra-allelic (or alfa) complementation with a defective form of LacZ encoded by a host carrying the mutation lacZ$\Delta$M15 (Messing et al., 1977, Proc. Natl. Acad. Sci. USA 74:3642-3646; Messing et al., 1981, Nucl. Acids Res. 9:309-321). In the presence of IPTG bacteria synthesize both oligopeptides and produce functional beta-galactosidase which metabolizes the indicator dye, 5-bromo-4-chloro-3-indolyl-beta-D-galactoside (XGAL), resulting in blue colour of colonies. Insertion of foreign DNA into the multiple cloning site, which is located within the lacZ gene and replaces codons 6-7, disrupts the integrity of N-LacZ and abolishes alfa-complementation. Therefore, bacteria carrying recombinant plasmids give rise to white colonies. This so-called "blue/white" screening is advantageous compared to the negative selection described in previous section as it allows direct visualization of recombinants.

The approach of positive selection is also based on insertional inactivation of a gene located within the cloning vector. However, in contrast to cloning vectors described above, the latter gene is toxic to the host. Therefore, host cells with uncut or self-ligated (empty) molecules of positive selection cloning vector cannot grow. As a result, only those cells that contain recombinant plasmids with the foreign DNA fragment inserted within the toxic gene will grow and form colonies.

There is a large variety of positive selection cloning vectors. For instance, a recent review by C. Young-Jun et al. describes 72 positive selection cloning vectors which could be classified into five groups according to the function of the genes and the mechanisms for direct selection (Critical Reviews in Biotechnology, 22, 225-244 [2002]): (1) compound dependence; (2) depression of antibiotic resistance gene; (3) lethal gene; (4) palindrome; (5) restriction/modification system.

Recombinant plasmids, obtained after insertion of foreign DNA fragment into the cloning vector, are very often used as DNA sources for subsequent cloning into final vectors which are suitable for specific downstream applications. Sub-cloning takes time and is labour consuming. Thus, cloning vectors are improved by adding various genetic elements which have the potential to expand their range of downstream applications directly, without further subcloning steps. For instance, incorporation of an additional replication region, obtained from E. coli filamentous phages f1 or M13, provides the possibility of isolate recombinant plasmids in a single-stranded form (Dente, L., Cesareni, G., Cortese, R. Nucleic Acids Res., 1983, 11, 1645-1655). Addition of the second replication region, which is functional in the other organism, converts such a vector into a shuttle vector and enlarges the host range (Macrina F L., et al. Gene. 1982; 19:345-53). The incorporation of a DNA sequence which is responsible for mobilization function provides an opportunity to transfer such a plasmid from one host to the other through conjugation (Mongkolsuk S., et al. Gene. 1994; 143:145-6).

Perhaps the most popular downstream application of recombinant plasmids, however, is in vivo and in vitro synthesis of proteins encoded by cloned genes as well as in vitro production of high levels of RNA transcripts of cloned DNA inserts. The preferred promoter which may be used in all three applications is the bacteriophage T7 promoter (Studier and Moffatt J Mol. Biol. 1986; 189:113-30; Mead, D. A., et al., Protein Eng. 1986 1: 67-74). Due to its versatility the T7 promoter was inserted into many "blue/white" cloning vectors, including, but not limited to, pBluescript II (Alting-Mees M A, and Short J M Nucleic Acids Res. 1989; 17:9494.), pTZ series (Mead, D. A., Szczesna-Skorupa, E., Kemper, B. Protein Eng. 1986 1: 67-74), pGEM series (Promega Corporation), LITMUS series (New England Biolabs), and also into several positive selection cloning vectors, including, but not limited to, pCR-Blunt, pZEro-1, pZEro-2 (Invitrogen Co., CA, USA).

Inspection of cloning vectors listed above revealed that T7 promoter in all cases is inserted into the gene for N-LacZ next to the multiple cloning site (to ensure positive selection, toxic gene ccdB was fused to that coding for N-LacZ in positive selection cloning vectors pCR-Blunt, pZEro-1 and pZEro-2). Insertion of foreign DNA into the cloning site interrupts synthesis of encoded product, allowing identification of clones carrying recombinant plasmids either by "blue/white" screening (pBluescript II, pTZ series, pGEM series, LITMUS series) or by their direct selection (pCR-Blunt, pZEro-1, pZEro-2).

However, the structure of cloning vectors based on insertional inactivation of N-LacZ is not optimal for cloning and may lead to false-negative results (Close T J., et al. Gene. 1983; 23:131-6). As mentioned above, multiple cloning sites in these vectors replaces the $6^{th}$ and $7^{th}$ codon of N-LacZ. The N-terminal amino acid residues, encoded by codons from 1 to 7, are not essential for beta-galactosidase activity, thus at least three types of DNA fragments may result in functional beta-galactosidase after their insertion into the cloning site:

(1) DNA fragment without translation termination signals, when inserted in-frame. Insertions result in enlarged N-terminal fragments of LacZ which may be as active as the insertion-free one;

(2) DNA fragment which encodes open reading frame truncated at its 3'-terminus, when after cloning it becomes in-frame with lacZ;

(3) DNA fragment which provide signals to the truncated N-terminal fragment of beta-galactosidase required for translation reinitiation (any in-frame translation initiation codon AUG, GUG or UUG and the Shine-Dalgarno like sequence).

The two latter events result in production of N-LacZ fused to a foreign peptide, which often does not impair its activity. In case of "blue/white" cloning vectors such clones will produce blue colour and will be erroneously discarded as non-recombinants, whereas in case of positive selection vectors such clones will be toxic to the host and corresponding DNA fragments will be identified as "non-clonable".

Thus, a need exists for an improved cloning vector which is based on a configuration which minimizes the generation of false-negative clones and which in addition contains a promoter, such as a T7 promoter, useful in many downstream applications close to the cloning site. In particular, such a vector should retain the feature of a positive selection cloning vector since these are superior in cloning experiments as they eliminate the background of parental non-recombinant vector molecules.

Accordingly, the present invention provides a vector for transformation into a host cell comprising a toxic gene encoding a product that is lethal to the host cell, wherein the toxic gene comprises:

an essential sequence region whose integrity is necessary in order for the encoded toxic product to be lethal to the host cell;

an inessential sequence region whose integrity is not essential in order for the encoded toxic gene to be lethal to the host cell;

a regulatory sequence inserted in-frame into the inessential sequence region; and a cloning site within the essential sequence region for insertion of a nucleic acid sequence, wherein the regulatory sequence and the cloning site are positioned so as to allow the regulatory sequence to be operably linked to a nucleic acid sequence when the nucleic acid sequence is inserted into the cloning site.

In one embodiment of the present invention the toxic gene of the vector encodes a nuclease. Preferably the nuclease is a restriction enzyme. Most preferably the restriction enzyme is eco47IR.

The regulatory sequence of the vector is preferably a promoter sequence. Most preferably the regulatory sequence is a T7 promoter sequence.

In a particularly preferred embodiment of the vector of the present invention the toxic gene is eco47IR, the regulatory sequence is a T7 promoter sequence, the cloning site is an Eco32I site and the vector further comprises a replication region and an ampicillin resistance gene.

The present invention also provides a recombinant host cell or a kit comprising the vector of the present invention.

Still further, the present invention provides a method for producing a vector suitable for cloning nucleic acid molecules and transformation into a host cell comprising the steps of:

a) selecting a vector comprising a toxic gene encoding a product that is lethal to the host cell; and b) inserting a regulatory sequence into the sequence of the toxic gene at an inessential region of the toxic gene whose integrity is not essential in order for the encoded toxic gene product to be lethal to the host cell;

wherein the sequence of the toxic gene further comprises a cloning site at a region within the sequence of the toxic gene whose integrity is essential in order for the product encoded by the toxic gene to be lethal to the host cell.

In a preferred embodiment of this method, the cloning site is introduced into the toxic gene by site specific mutagenesis.

The present invention also provides a vector as described above in which a nucleic acid molecule has been cloned into the toxic gene at the cloning site. Similarly a method of cloning a nucleic acid molecule is provided comprising the steps of:
a) cutting a vector as described above at the cloning site to create a linearized vector; and
b) ligating the nucleic acid molecule into the linearized vector to form a circularised vector product.

The vector of the present invention can be used for the in vitro expression of a nucleic acid molecule and for non-therapeutic in vivo expression of a nucleic acid molecule.

The present inventors have surprisingly found that the vector of the present invention overcomes the problems of the prior art. In particular, the cloning of even a small nucleic acid molecule into the cloning site disrupts the integrity of the toxic gene and ensures the positive selection of a host cell containing the recombinant vector. Further, the presence of an efficient regulatory sequence, such as a promoter, operably linked and preferably next to the cloning site enables the recombinant vector to be employed directly for downstream applications, including inducible expression of cloned genes in vivo and for transcription of cloned DNA fragments in vitro without further DNA manipulations.

The ability of the vector of the present invention to be used in methods of positive selection is based on the technique of insertional inactivation of the toxic gene located within the vector. In particular, if the integrity of the toxic gene is maintained, when the vector is transformed into a host cell type which is susceptible to the toxic product from the gene, the presence of the toxic gene will be lethal to the host cell. Therefore, host cells with uncut or self-ligated (empty) molecules of positive selection cloning vector of the present invention cannot grow. If, however, during the cloning process a nucleic acid molecule is ligated into the cloning site within the toxic gene, the integrity of the gene is disrupted and the vector is no longer capable of producing a functional toxic product. When such a vector is transformed into a host cell type susceptible to the toxic product from the gene, the host cell will survive and grow because no functional toxic product is being produced from the vector. Accordingly, in a cloning method, only those host cells that contain recombinant vectors with the foreign nucleic acid molecule or fragment inserted within the toxic gene will grow and form colonies.

The vector to which the present invention can be applied is not particularly limited. The vectors can be DNA vectors, which may be single stranded or double stranded. Example vectors to which the present invention can be applied include plasmids, bacteriophages, bacterial artificial chromosomes, and yeast artificial chromosomes. In a preferred embodiment of the invention the vector is a plasmid.

The host cell to which the present invention can be applied is also not particularly limited and can be any of the host cell types commonly used in the field of technology of the present invention for the cloning and expression of recombinant genes. In particular the host cell is one which allows propagation of the vector and growth of vector numbers. The cell may be a eukaryotic or a prokaryotic cell. Particular examples of suitable prokaryotic host cells are bacterial cells from the genus *Escherichia* and *Bacillus*.

A toxic gene according to the present invention is one whose product is lethal to a host cell. As described above, the toxic gene allows the vector of the present invention to be used in a positive selection cloning method. If during the cloning method a nucleic acid molecule fails to be inserted into the vector, and the linearized vector simply re-ligates restoring the integrity of the toxic gene and creating an 'empty vector', subsequent expression of the toxic gene in a host cell will be lethal to that host cell. Thus host cells containing these 'empty vectors', when cultured under conditions which usually permit the expression of the toxic gene, will not survive.

The nature of the toxic gene is not particularly limited. The toxic gene may be one whose product is a nuclease, such as a restriction enzyme, typically a restriction endonuclease. Such genes are lethal to host cells because the functional gene product, i.e. the restriction endonuclease, is an enzyme which will destroy the host cell DNA. Alternatively, the toxic product may simply bind the host cell DNA and prevent it from being expressed or replicated.

Other examples of suitable, known toxic genes and their mechanism of action are given in the following references:

Saïda F, Uzan M, Lallemand J Y, Bontems F. New system for positive selection of recombinant plasmids and dual expression in yeast and bacteria based on the restriction ribonuclease RegB. Biotechnol Prog. 2003 May-June; 19(3):727-33. This reference describes the coupling of toxic restriction endoribonuclease RegB, from the bacteriophage T4, to the prokaryotic T7 and the eukaryotic GAL1 promoters, to construct a two-function plasmid called pTOXR-1. This plasmid is a zero-background cloning vector. It allows an efficient positive selection of recombinant plasmids without the need to completely digest, dephosphorylate, or purify the vector prior to the ligation step. The pTOXR-1 positive selection system requires no special *Escherichia coli* strains, no special culture media, and no addition of inducer to the selective plates.

Yazynin S, Lange H, Mokros T, Deyev S, Lemke H. A new phagemid vector for positive selection of recombinants based on a conditionally lethal barnase gene. FEBS Lett. 1999 Jun. 11; 452(3):351-4. This reference describes a phagemid cloning vector for positive selection of recombinants, pBa-7, which contains an active barnase gene encoding the cytotoxic ribonuclease from *Bacillus amyloliquefaciens*, under control of the lac promoter. PBa-7 is a derivative of the high-copy number pBluescript II KS+ phagemid in which the modified barnase killer gene has been fused downstream from the lac promoter of the pBluescript II KS+ multiple restriction site. When a lacIq-negative *Escherichia coli* strain is transformed by this vector, the active barnase blocks bacterial growth by massive RNA destruction. However, if barnase is inactivated by insertion of a foreign DNA fragment into the multirestriction site of the vector, this recombinant plasmid no longer interferes with the host viability.

Schlieper D, von Wilcken-Bergmann B, Schmidt M, Sobek H. Müller-Hill B. A positive selection vector for cloning of long polymerase chain reaction fragments based on a lethal mutant of the crp gene of *Escherichia coli*. Anal Biochem. 1998 Mar. 15; 257(2):203-9. This reference describes a cloning vector with a tight positive selection for recombinant clones in *Escherichia coli*. The positive selection pressure results from a lethal mutation within the *E. coli* gene coding for the catabolite gene activator protein CAP, which is disrupted whenever a fragment is successfully inserted.

Henrich B, Schmidtberger B. Positive-selection vector with enhanced lytic potential based on a variant of phi X174 phage gene E. Gene. 1995 Feb. 27; 154(1):51-4). This reference discloses a cloning vector, pUH89, allowing positive selection of recombinant *Escherichia coli* clones by insertional inactivation of the modified lysis gene E of bacteriophage phi X174.

The toxic gene can be expressed by a second promoter located in the 5' region upstream of the start codon of the toxic gene. In some cases the promoter can be an inducible promoter that allows expression of the toxic gene only in inducing conditions. An example of a suitable inducible promoter is a tightly repressible hybrid promoter, like the ones described by Lutz R., and Bujard H. (Independent and tight regulation of transcriptional units in *Escherichia coli* via the LacR/O, the TetR/O and AraC/I1-I2 regulatory elements. Nucleic Acids Res. 1997 Mar. 15; 25(6):1203-10).

In other cases where the second promoter is non-inducible (or is inducible, but is not tightly regulated, such as the lac promoter that promotes expression in the presence of IPTG) the vector according to the present invention can be propagated in a host cell that is not susceptible to the toxic product of the gene. For example, where the toxic gene is eco47IR, which produces the restriction enzyme Eco47I, the vector can be propagated in the *E. coli* wild-type strain RFL47 which is a natural producer of Eco47I, or in a host cell which contains a plasmid with a functional gene for Eco47II methyltransferase. During the process of cloning of nucleic acid molecules by positive selection, a non-susceptible host cell type can be exchanged for one which is susceptible to the toxic product of the gene.

In a preferred feature of the invention, expression of the toxic gene is driven by the lac promoter, more preferably $P_{lacUV5}$ which is a modified $P_{lac}$ promoter which provides expression of the toxic gene without IPTG induction.

According to the present invention the sequence of the toxic gene is divided into those regions whose integrity is essential in order for the encoded toxic product to be lethal to the host cell and those regions whose integrity is non-essential for the encoded toxic product to be lethal to the host cell. For instance, positive selection cloning vectors pGATA (Trudel P., et al. Biotechniques. 1996; 20:684-93) and pMT440 (Yazynin S A., et al. Gene. 1996; 169:131-2) contain multiple cloning sites which are inserted into the structural part of toxic genes at positions of external loops. The surface-located protein regions, and especially loops, may tolerate insertions of short oligopeptides (Manoil C., and Bailey J., J. Mol. Biol., 267, 250-263) or even full-length proteins (Biondi R. M., et al. Nucleic Acids Res., 26, 4946-4952).

In the present invention inessential regions are those regions of the sequence which encode sections of the toxic product which will tolerate the insertion of additional amino acid residues. For example, in a restriction enzyme or a DNA binding protein the inessential regions may be those which code for loops in the protein away from the protein's active site or binding site. Accordingly, when the regulatory sequence is inserted in-frame into the toxic gene sequence the lethal nature of the toxic product is not affected. In contrast, essential regions are those regions of the sequence which encode sections of the toxic product which do not tolerate the insertion of additional amino acid residues. Such regions are structurally important regions of the toxic product that are essential for folding (i.e. maintaining the structure of the product) and function. They include those regions encoding amino acid residues essential for function of the active side or binding site of the protein, such as those residues located in the active site or binding site, as well as those which are necessary for the formation of functional secondary, tertiary or quaternary protein structure (such regions usually comprise much more amino acids than those involved in active or binding sites formation). Accordingly, even an in-frame insertion of sequence into the cloning site in an essential region will prevent the toxic product from being lethal to the host cell.

In a particularly preferred aspect of the invention an essential region is one which encodes a section of the toxic product which does not tolerate the insertion of even a single extra amino acid residue. Thus the vector of the present invention allows the cloning and positive selection of even very small nucleic acid molecules, for example between 6 and 100 bp in length. In a particularly preferred embodiment of the invention the vector is capable of accepting inserts or nucleic acid sequence from 6 bp to 10 kb in length in a positive cloning selection method.

Those skilled in the art will be aware of the techniques in the art used to identify essential and inessential regions of the toxic gene (e.g. Manoil and Bailey, J. Mol. Biol., 267, 250-263; and Biondi et al., Nucleic Acids Res., 26, 4946-4952).

In a particularly preferred aspect of the present invention the regulatory sequence within the toxic gene is T7 promoter sequence. However, the invention can be applied with any regulatory sequences, including any promoter sequence, which is capable of being introduced into the toxic gene sequence at an inessential region without disrupting toxic product function. Suitable promoters for RNA synthesis/in vivo transcription could be: T7, SP6 and T3, PL and PR promoters from phage lambda, ParaBAD, Plac promoter and its various derivatives, such as Ptac, PlavUV5, etc. without controlling/operators sequences. The promoter, inserted into the toxic gene at a position which tolerates such insertion, may be combined with additional features including, but not limited to, an additional regulatory element, a ribosome binding site, a nucleotide sequence encoding protein purification tag, and/or an additional restriction endonuclease site convenient for subcloning. The regulatory sequence and additional features are capable of causing, controlling, promoting or driving the expression of a nucleic acid sequence once it is inserted into the cloning site of the vector of the present invention.

The cloning site in the vector of the present invention may be one or more cloning sites. Further, it may be a multiple cloning site. The specific cloning site(s) used in the present invention is not particularly limited but may be any cloning site(s) known in the art, for example any restriction endonuclease site. Preferably the cloning site is a recognition sequence for a restriction endonuclease which cuts the gene to create either blunt or sticky ends. Most preferably the restriction endonuclease cuts the gene to create blunt ends, for example Eco32I.

In the vector of the present invention the regulatory sequence and the cloning site are positioned so as to allow the regulatory sequence to be operably linked to a nucleic acid sequence when the nucleic acid sequence is inserted into the cloning site, i.e. the regulatory sequence is capable of expressing a nucleic acid sequence inserted into the cloning site. Preferable the regulatory sequence is in the close vicinity of the cloning site. More preferably the 5' end of the regulatory sequence, typically a promoter sequence, is within 150 base pairs of the cloning site.

The vector of the present invention may contain additional features including, but not limited to, one or more selectable marker genes such as antibiotic resistance genes, a phage origin of replication, additional promoter, and/or a transcription terminator. A preferred antibiotic resistance gene is bla, which encodes β-lactamase conferring resistance to ampicillin. A preferred origin of replication is rep(pMB1) which is a replicon from the pMB1 plasmid.

The vector according to the present invention can be in circular or linear form. Where the vector is in linear form it can have blunt or sticky ends. In particular the linear blunt ended vector can be formed by cutting the vector with an enzyme that cuts at the cloning site to generate blunt ends.

The invention further provides a recombinant host cell comprising a vector according to the present invention with a nucleic acid molecule inserted into the cloning site. In this embodiment, the host cell type can be any of those as described above.

The present invention further provides a kit for cloning of nucleic acid molecules or fragments. The kit comprises a vector according to the present invention, preferably the vector has been linearized by cutting it with a restriction endonuclease at the cloning site and is blunt ended. In a preferred embodiment the kit is a cloning kit capable of being used to clone a plurality of nucleic acid sequences. Most preferably the plurality of nucleic acid sequences is generated by PCR. For these purposes the kit further comprises one or more of the following: a reaction buffer, a DNA ligase, a DNA blunting enzyme, nuclease free water, a control PCR product with 3' dA overhangs which can be used as a control in the cloning of PCR products into the vector of the present invention, and forward and reverse sequencing primers, which can be used to sequence a nucleic acid sequence once it has been cloned into the vector of the present invention. In particular, the DNA blunting enzyme can be one which is capable of blunting PCR products with 3'-dA overhangs generated using Taq DNA polymerase or other non-proofreading thermostable DNA polymerases.

The present invention further provides a method for producing a vector suitable for cloning nucleic acid molecules and transformation into a host cell comprising the steps of:
  a) selecting a vector comprising a toxic gene encoding a product that is lethal to the host cell; and
  b) inserting a regulatory sequence into the sequence of the toxic gene at an inessential region of the toxic gene whose integrity is not essential in order for the encoded toxic gene product to be lethal to the host cell;
  wherein the sequence of the toxic gene further comprises a cloning site at a region within the sequence of the toxic gene whose integrity is essential in order for the product encoded by the toxic gene to be lethal to the host cell.

The cloning site may occur in the toxic gene naturally or may be introduced by means of site-specific mutagenesis.

Further, the vector to which the method may be applied may be any vector known in the art. In particular, it may be one which already contains a toxic gene, such as, for example, the plasmid pJET1.

The present invention further provides a method of cloning a nucleic acid molecule comprising the steps of:
  a) cutting a vector according to the present invention at the cloning site to create a linearized vector; and
  b) ligating the nucleic acid molecule into the linearized vector to form a circularised vector product.

In particular, the vector of the present invention can be used in positive selection cloning techniques known in the prior art.

As described above, once a nucleic acid molecule has been inserted into the vector of the present invention it can be used directly for expression of the molecule in vitro. In particular, this can be useful to produce quantities of the product of the nucleic acid molecule for experimental and research purposes or for commercial sale of the product.

Further, once a nucleic acid molecule has been inserted into the vector of the present invention it can be used directly for non therapeutic in vivo expression, for example in in vivo laboratory studies.

In particular, the vector of the present invention facilitates the cloning of PCR fragments and enables preliminary downstream characterisation of the product encoded by the cloned fragments.

In a specific embodiment the present invention provides an improved positive selection cloning vector pJET1-3A which contains: (i) replication region, (ii) ampicillin resistance gene, (iii) toxic gene eco47IR for positive selection, (iv) T7 promoter sequence inserted into the toxic gene at position which tolerates such insertion, and (v) cloning site within the toxic gene at position where even smallest insertion inactivates the toxic product.

The improved positive selection cloning vector pJET1-3A allows positive selection of clones containing the inserted foreign DNA fragment with minimal background and provides possibility to use recombinant molecules directly in downstream applications including, but not limited to, protein expression in vivo and in vitro and synthesis of high levels of RNA transcripts of cloned DNA inserts in vitro.

The invention will now be described by way of example only, with reference to the following experiments and specific embodiments, and the accompanying drawings in which:

FIG. 1 illustrates the structure of synthetic Mu transposon Tn-Km-Mre (1430 bp), which was used to generate random insertions of 21 nucleotides into the structural part of eco47IR gene (SEQ ID No: 1-3'-5' sequence shown). Transposon contains gene Kan, which confers resistance to antibiotic kanamycin. Tn-Km-Mre starts and ends with the inverted sequence, which is identical to the right end of the Mu phage genome (except trinucleotide GCG shown in lower-case which replaced the original sequence CTT in order to create MreI target), including the R1 and R2 MuA binding sites (Savilahti et al.). Bold letters show nucleotides remaining at the position of transposon insertion after removal of transposon by MreI cleavage followed by blunting with polymerase and ligation.

Figure 2:
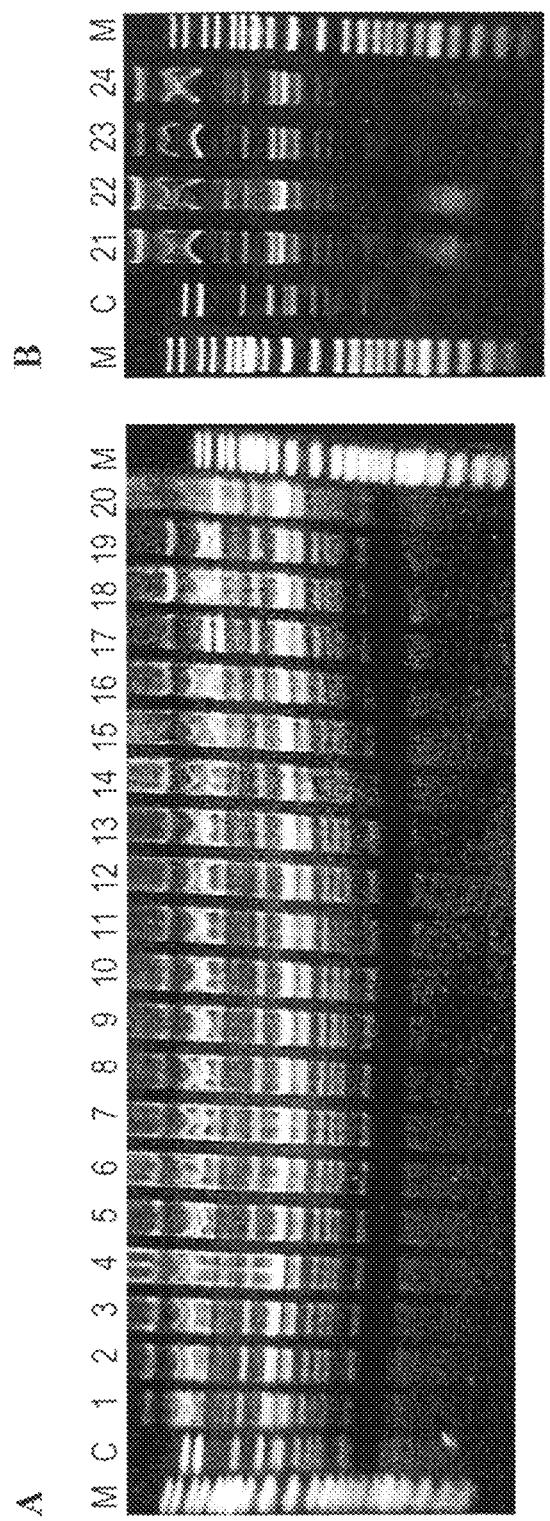
Figure 3:
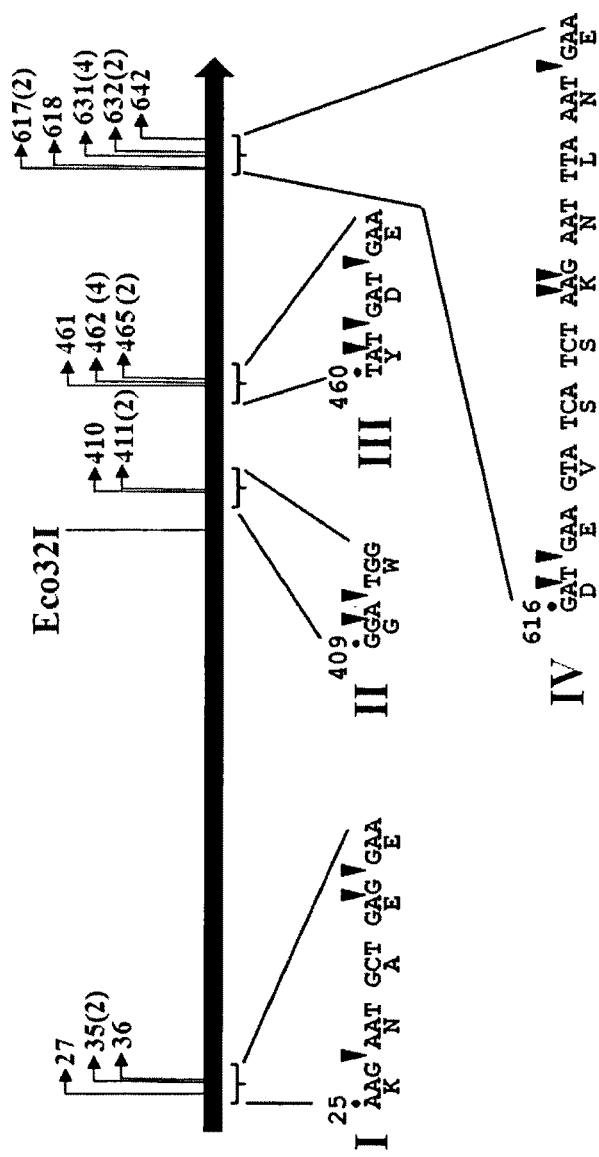

FIG. 2 shows digestion products of phage λ DNA by crude cell extracts of Eco47I mutants able to restrict phage λ propagation. (A), λ DNA incubated with crude extracts prepared from cells expressing mutant proteins through 1 to 20; (B), λ DNA incubated with crude extracts prepared from cells expressing mutant proteins through 21 to 24. M—molecular weight marker GeneRuler™ DNA Ladder Mix. C—λ DNA digested with Eco47I FIG. 3 shows linear structure of restriction endonuclease Eco47I and protein regions from I to IV, which accept insertion of 7 amino acid residues retaining the ability of mutants to restrict phage lambda propagation (SEQ ID Nos: 2 and 10—the nucleotide sequence and the amino acid sequence shown for region I, respectively; SEQ ID Nos: 3 and 11—the nucleotide sequence and the amino acid sequence shown for region IV). Thin arrows, numbers and black triangles show nucleotide positions of eco47IR gene after which insertions in 24 isolated mutants were identified. Numbers in parenthesis indicate the number of identified mutants carrying the same mutation. The Eco32I target suitable for the cloning of blunt-ended DNA fragments is also shown.

Figure 4:
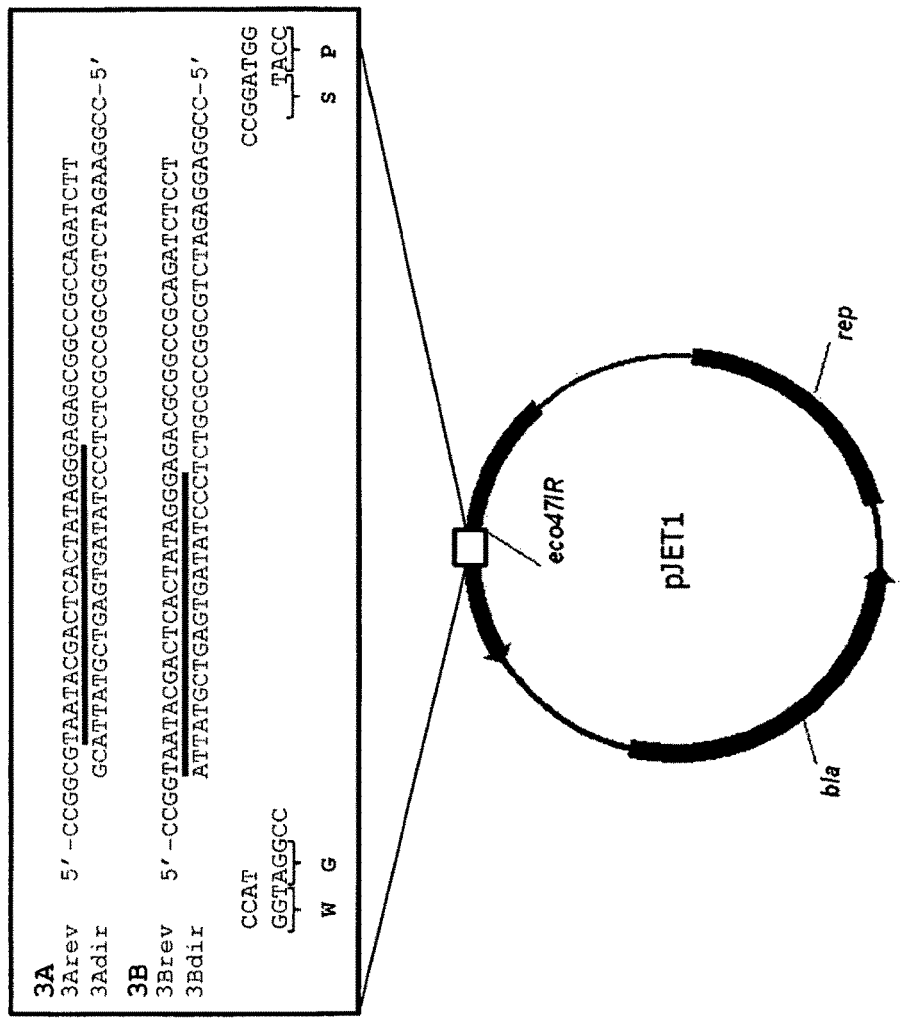

FIG. 4 shows a scheme of insertion of oligoduplexes 3A and 3B into the Kpn2I-linearized positive selection cloning vector pJET1 (SEQ ID No: 4-3Adir; SEQ ID No: 5-3Arev; SEQ ID No: 6-3Bdir; SEQ ID No: 7-3Brev). Underlined nucleotides represent the consensus sequence of phage T7 promoter. Amino acid residues GW shown below the nt sequence represent region II of R.Eco47I which tolerates insertions. bla, gene coding for β-lactamase which confers resistance to antibiotic ampicillin. rep, DNA region responsible for plasmid replication.

Figure 5:
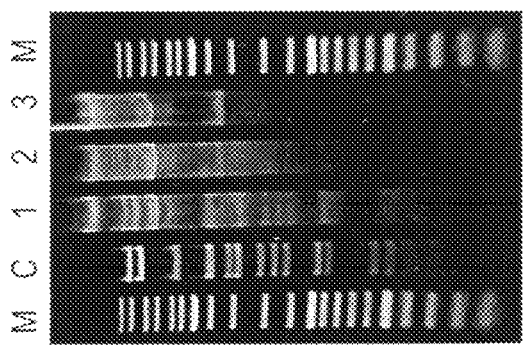

FIG. 5 shows restriction endonuclease activity of crude extracts prepared from methylation-proficient *E. coli* DH10B [pAC-Eco47IIM] cells, carrying: lane 1, pJET1; lane 2, pJET1-3A; lane 3, pJET1-3B. M—molecular weight marker GeneRuler™ DNA Ladder Mix. C—λ DNA digested with Eco47I.

Figure 6:
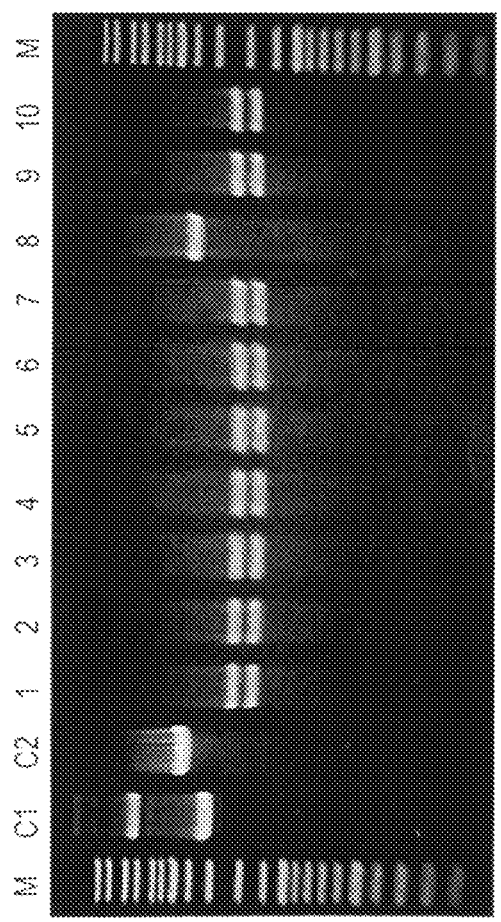

FIG. 6 illustrates the ability to positively select recombinant plasmids carrying the cloned 6-bp oligoduplex (which contains Cfr10I target) using pJET1-3A. Figure shows results of Cfr10I cleavage of plasmids, isolated from randomly picked transformants through 1 to 10. M—molecular weight marker GeneRuler™ DNA Ladder Mix. C1—pJET1-3A DNA, supercoiled. C2—pJET1-3A DNA digested with Cfr10I.

FIG. 7 shows the structure of primers used to amplify the gene for HphIMA methyltransferase. 1-HA primer (SEQ ID No: 8) contains ribosome binding site (grey box) and translation initiation codon (boxed). 2-HA primer (SEQ ID No: 9) encompasses the nt sequence (underlined) which is complementary to the translation termination codon TAA.

Figure 8:
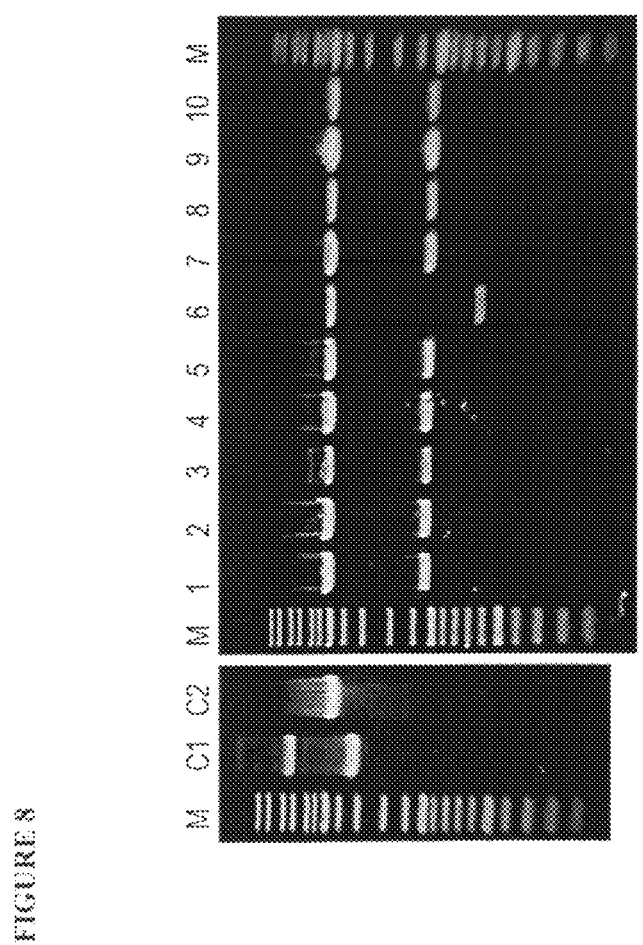

FIG. 8 illustrates the ability to positively select recombinant plasmids carrying the cloned 1040-bp DNA fragment (which codes for HphIMA methyltransferase) using pJET1-3A. Figure shows results of BglII cleavage of plasmids, isolated from randomly picked transformants through 1 to 10. M—molecular weight marker GeneRuler™ DNA Ladder Mix. C1—pJET1-3A DNA, supercoiled. C2—pJET1-3A DNA, linearized with Cfr10I.

Figure 9:
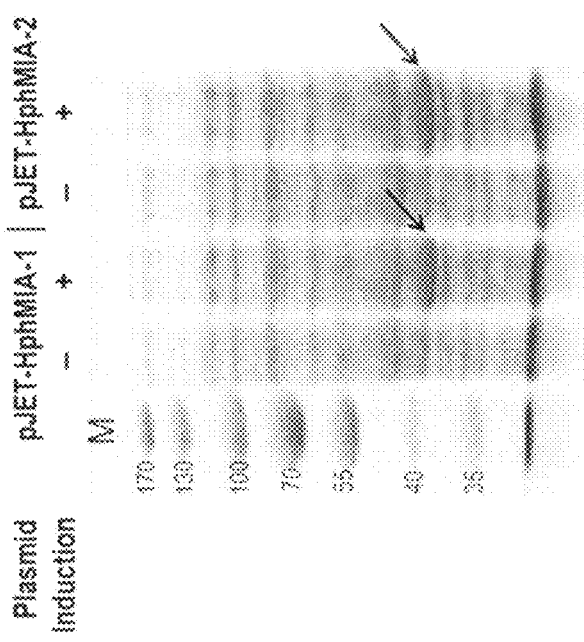

FIG. 9 illustrates in vivo functionality of the T7 promoter located within the positive selection vector pJET1-3A. Total proteins of *E. coli* ER2566 cells carrying either pJET-HphMIA-1 or pJET-HphMIA-2 and grown either with (+) or without (−) induction with IPTG were analysed. Arrows indicate protein bands, which appeared after the induction. M—PageRuler™ Prestained Protein Ladder. Numbers on the left side of the ladder indicate apparent molecular weights.

Figure 10:
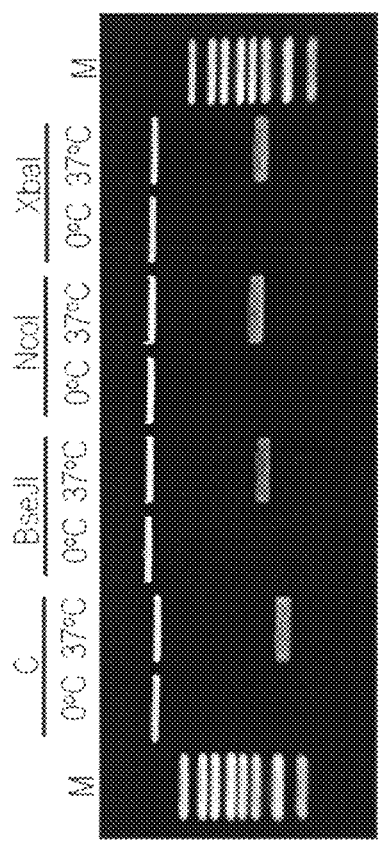

FIG. 10 illustrates in vitro functionality of the T7 promoter located within the positive selection vector pJET1-3A. Template DNA (JET-HphMIA-1) was separately linearized with BseJI, NcoI or XbaI and added to the T7 transcription kit. Then, reaction mixtures were incubated for 2 hours either at 37° C. or at 0° C. and analysed. C—control template included into the T7 transcription kit. M—molecular weight marker RiboRuler™ RNR Ladder, High Range.

In a specific embodiment of the present invention, the improved positive selection cloning vector pJET1-3A is provided which contains T7 promoter inserted into the toxic gene in protein region that accepts extra amino acid residues and does not prevent functional activity. The inserted promoter is located close to the restriction endonuclease target which may be used for cloning of any blunt-ended DNA fragment. The cloning site is located in protein region which does not tolerate even as small insertion as two amino acid residues. Such configuration of the cloning vector allows, in addition to the efficient cloning and positive selection, to use recombinant plasmids resulting after the insertion of foreign DNA fragment for inducible in vivo and in vitro expression of cloned genes as well as for in vitro transcription of cloned DNA fragments.

The vector described herein is an improvement to the positive selection cloning vector pJET1. Two major steps were carried out in order to construct the improved vector pJET1-3A. During the first step regions of the toxic gene, which tolerate small insertions were identified. In the second step synthetic DNA coding for the T7 promoter was inserted into one such region and resulting plasmid pJET1-3A tested for its cloning properties.

In the experimental disclosure which follows the following bacterial strains, phages, plasmids, media, enzymes, kits and markers were used:

Bacterial Strains Phages, Plasmids, Media and Transformation

*Escherichia coli* strain DH10B F− mcrA Δ(mrr-hsdRMS-mcrBC) φ80lacZΔM15 ΔlacX74 recA1 endA1 araD139 Δ(ara, leu)7697 galU galK λ− rpsL nupG (Invitrogen) was used as a host in cloning procedures, and strain ER2566 F− fhuA2 [lon] ompT lacZ::T7 gene1 gal sulA11 (mcrC-mrr) 114::IS10 R(mcr-73::miniTn10-TetS)2 R(zgb-210::Tn10) (TetS) endA1 [dcm] (New England Biolabs) was used in experiment of inducible expression. In order to protect the host DNA from degradation caused by expressed recombinant Eco47I restriction endonuclease, either the *E. coli* wild-type strain RFL47 (Fermentas), which is a natural producer of Eco47I restriction endonuclease (Janulaitis et al., FEBS Lett., 161 (1983) 213-216), or DH10B supplemented with pAC-Eco47IIM (Fermentas collection) was used. pAC-Eco47IIM is chloramphenicol-resistant plasmid, derived from pACYC184 (Chang and Cohen, J. Bacteriol. 134: 1141-1156, 1978), which contains functional gene for Eco47II methyltransferase (Stankevicius et al., Gene 1995). Phage λ$_{vir}$ (Fermentas collection) was propagated as described (Sambrook, J., Fritsch, E. F., and Maniatis, T. (1989) *Molecular Cloning: A Laboratory Manual*, 2$^{nd}$ Ed., Cold Spring Harbor Laboratory, Cold Spring Harbor, N.Y.). Plasmid pJET1 (GenBank Accession Number DQ317600) is a positive selection cloning vector commercially available from Fermentas UAB. Plasmid pJET-TnMreIMreI (Fermentas collection) carries the modified kanamycin-resistant mini-iMu transposon which is inserted into pJET1. The plasmid pET-AMVR-HphIA (Fermentas collection) contains gene coding for m6A-specific HphI methyltransferase which is inserted into the expression vector pET-21b (Novagen). All strains were grown in LB medium containing ampicillin (Ap, 100 mg/l), kanamycin (Km, 50 mg/l) and/or chloramphenicol (Cm, 30 mg/l) as required. Cells were transformed using the CaCl$_2$-heat shock method (Sambrook, 1989) or by electroporation. Transformants were selected by plating onto LB agar supplemented with appropriate antibiotics.

Enzymes, Kits, Markers

All enzymes, kits and molecular weight markers and other reagents, unless indicated otherwise, were from Fermentas. All enzymatic reactions were performed according to the manufacturer's instructions.

Experimental Outline

To develop the vector described in this invention, first of all it was necessary to identify sites of the toxic gene eco47IR tolerating insertion of additional amino acid residues, and then to explore this information for rational insertion of synthetic DNA encompassing the T7 promoter into the structural part of eco47IR. There is no structural information on Eco47I used in this study. However, the alternative transposon-based approach may be used to identify protein sites which tolerate relatively short in-frame insertions without loss of function (Manoil C., Traxler B., Methods, 2000, 20(1), 55-61). This approach is based on random mutagenesis of gene under investigation by transposon, which contains targets of the rare-cutting restriction enzyme within (or close to the) terminal inverted repeats. In the next step pooled transposon-carrying plasmids are cleaved with the aforementioned restriction enzyme and resulting linear DNA molecules are self-ligated. After deletion of the transposon body from plasmids a fixed number of nucleotides at the position of each transposon insertion remain, resulting in collection of mutants carrying random insertions of the same size. In the next step those mutants that preserve wild-type function need to be identified. Previously it was noticed that the cloned Eco47I-II restriction-modification system ensures resistance of the host to the phage $\lambda_{vir}$ infection (Stankevicius et al., Gene 1995), and we used this feature to isolate those insertional mutants, which protect host cells from phage propagation. Two dozen of isolated mutants were analyzed in order to identify R.Eco47I protein sites permissive for insertions, and one out of four identified permissive sites was used to insert a synthetic duplex DNA oligonucleotide (promoter cassette).

Random Transposon Mutagenesis of Positive Selection Gene Eco47IR

Random mutagenesis of eco47IR gene, located within the positive selection cloning vector pJET1, was done by in vitro transposition using (i) linear transposon Tn-Km-Mre (designed and constructed at Fermentas) which was excised from its carrier plasmid pJET-TnMreIMreI with the restriction endonuclease BglII (FIG. 1), and (ii) MuA transposase isolated from recombinant E. coli strain at Fermentas. As shown in FIG. 1, three nucleotides were changed in both inversely oriented right-end (R end) segments of phage Mu that flank the kanamycine resistance gene during the construction of Tn-Km-Mre. This mutation does not have the impact on transposition efficiency and results in appearance of MreI targets which may be used to cleave transposon out. In case if plasmid carrying the inserted Tn-Km-Mre is cleaved with MreI, resulting cohesive DNA ends are filled-in with polymerase and linear blunt fragments are self-ligated, 8 nucleotides from each end of the transposon remain within the structure of resulting plasmid. Taken together with 5 nucleotides which appear after duplication of the target site (Allet, B. 1979. Mu insertion duplicates a 5 base pair sequence at host inserted site. Cell 16:123-129) all these manipulations result in random insertion of 21 extra nucleotides which may be translated into 7 amino acids in the encoded protein.

Transposition In Vitro Reaction Mixture (40 µl) was Prepared by Mixing Following Components:

8 µl 5× Reaction Buffer (125 mM Tris-acetate, pH 8.0, 600 mM NaCl, 50 mM Mg acetate, 5 mM DTT, 0.25% Triton X-100, 50% Glycerol, 100 mg/ml BSA)
2 µl pJET1 DNA (concentration: 270 ng/µl)
26 µl water, nuclease free
2 µl DNA of linear transposon Tn-Km-Mre (concentration: 50 ng/µl)
2 µl transposase MuA (concentration: 250 ng/µl)

Reaction mixture was incubated at 30° C. for 1 h and then transposase was inactivated by heating at 75° C. for 10 min. Recombinant DNA was precipitated with ethanol following standard procedures (Sambrook, J. 1989) and dissolved in 10 µl of water (nuclease free). 2 µl of dissolved DNA was electroporated into 40 µl of E. coli DH10B electrocompetent cells and spread onto several LB-agar plates supplemented with ampicillin and kanamycin. Plates were incubated overnight at 37° C. Transformation resulted in ~4×10$^5$ colonies. Due to the toxicity of restriction endonuclease gene eco47IR located within pJET1 it was expected that all transformants will contain recombinant plasmids with the transposon-inactivated eco47IR gene.

Generation of 21 nt Insertions within the eco47IR Gene

Cells of resulting transformants were scrapped from the surface of LB-agar plates, centrifuged and DNA of their plasmids isolated using alkaline lysis approach (Sambrook, J. 1989) followed by additional purification with the Gene-JET Plasmid Miniprep Kit (Fermentas). The portion of isolated total plasmid DNA was cleaved with MreI. The completeness of cleavage reaction was monitored by agarose gel electrophoresis of reaction products. After the reaction was complete (supercoiled DNA was converted into two linear DNA fragments, of which 1.4 kb corresponds to the excised transposon and 3.1 kb fragment corresponds to the vector backbone), restriction endonuclease was heat-inactivated and cohesive DNA ends blunted using Klenow fragment. Then the latter was heat-inactivated and 45 ng of linear blunt-ended DNA molecules were self-ligated in 50 µl of reaction mixture using 5 units of T4 DNA ligase. Ligation mixture was used to transform E. coli DH10B [carrying pAC-Eco47IIM plasmid encoding Eco47II methyltransferase capable of protecting host cell DNA from Eco47I restriction endonuclease action] cells using the $CaCl_2$-heat shock method. Transformation mixture was spread onto several LB-agar plates supplemented with ampicillin and chloramphenicol. Plates were incubated overnight at 37° C. Transformation yielded ~5000 transformants.

Identification of eco47IR Regions which Tolerate Insertion of 21 nt Preserving Functional Activity In order to identify functionally active mutants, biological selection procedure was applied (Mann, M. B., Rao, R. N. and Smith, H. O. (1978) Gene, 3, 97-112). This method is based on the acquired resistance of E. coli cells harboring a cloned restriction-modification system to infection by phage $\lambda_{vir}$. 1000 transformants were printed in parallel onto two LB-agar plates, one of which contained the top layer (Sambrook, J. 1989) supplemented with phage $\lambda_{vir}$ particles (10$^7$ per plate). Plates were incubated overnight at 37° C. Approximately 10% of tested clones survived phage infection, suggesting that they produce functionally active restriction enzyme. To test this, crude cell extracts of 24 positives were prepared according to the slightly modified procedure described by Whitehead and Brown (Whitehead, P. R. and Brown, N. L. (1985) Arch. Microbiol., 141, 70-74). The endonucleolytic activity of crude cell extracts was evaluated by incubating 2 µl of extract with 1 µg of λ DNA at 37° C. for 1 h in a 40 µl reaction mixture containing 10 mM Tris-HCl, pH8.5 at 37° C., 10 mM $MgCl_2$, 100 mM KCl and 0.1 mg/ml bovine serum albumin. Reaction products were analyzed by electrophoresis in 0.8% agarose gels. As expected, all 24 clones revealed Eco47I activity (FIG. 2). In order to find out the exact position of insertions, plasmid DNAs were isolated from 24 mutants and sequenced using standard forward and reverse pJET1 sequencing primers Analysis of sequencing results showed that insertions are distributed not randomly and can be grouped into four groups (FIG. 3). Such non-random distribution allowed us to suggest that each group represents distinct protein region which tolerates insertions. It is well known that surface-located loops may tolerate insertions of short oligopeptides, thus we concluded that identified Eco47I regions most likely form external loops that are not important for functioning.

Insertion of T7 Promoter into the Positive Selection Gene eco47IR

As described above, we identified four eco47IR regions which tolerate small insertions preserving the ability of mutant proteins to restrict propagation of phage lambda. The endonucleolytic activity of mutants was not very high, but enough to kill host cells in the absence of protective methylation. This feature is obligate for positive selection. Basing on these observations we concluded that all four positions may serve as targets for insertion of additional beneficial sequence elements. In case if tertiary structure of the toxic protein is available or can be modeled by computational approaches, persons skilled in the art may identify such tolerant candidate positions by identifying surface-located protein regions and especially loops. These regions have a potential to be used for insertion of additional sequence elements that may be useful in various downstream applications.

Of four identified eco47IR regions the second one is located very close to the multiple cloning site of positive selection vector pJET1. Shorter distance between cloning site and useful sequence features like additional restriction enzyme targets (for mapping and subcloning) or promoter (for in vivo and/or in vitro transcription) is beneficial. Thus we attempted to insert additional sequence elements into the $2^{nd}$ region of the eco47IR gene. Construction of improved positive selection cloning vectors pJET1-3A and pJET1-3B was initiated by linearization of the parent vector pJET1 with the restriction enzyme Kpn2I which target overlaps the $2^{nd}$ tolerant region of eco47IR (FIG. 4). The linearized vector was then treated with CIAP phosphatase in order to prevent self-ligation. After heat-inactivation of CIAP the linear dephosphorylated vector was ligated in parallel with two alternative duplex DNA oligonucleotides 3A and 3B which were made by annealing of complementary oligonucleotides 3Arev/3Adir and 3Brev/3Bdir, respectively (FIG. 4).

```
3Adir
                                          (SEQ ID No: 4)
5'CCGGAAGATCTGGCGGCCGCTCTCCCTATAGTGAGTCGTATTACG 3'

3Arev
                                          (SEQ ID No: 5)
5'CCGGCGTAATACGACTCACTATAGGGAGAGCGGCCGCCAGATCTT 3'

3Bdir
                                          (SEQ ID No: 6)
5'CCGGAGGAGATCTGCGGCCGCGTCTCCCTATAGTGAGTCGTATTA 3'

3Brev
                                          (SEQ ID No: 7)
5'CCGGTAATACGACTCACTATAGGGAGACGCGGCCGCAGATCTCCT 3'
```

Both duplexes contain T7 promoter sequence and targets for NotI and BglII, but in different reading frame. Prior to annealing step all four oligonucleotides were treated with T4 Polynucleotide kinase in order to phosphorylate their 5' ends. 3A and 3B duplexes were inserted into the Kpn2I site of pJET1 while regenerating the Kpn2I site on one side of the inserted oligoduplex but destroying it at the other side (FIG. 4). *E. coli* DH10B [pAC-Eco47IIM] cells were transformed with the ligation mixture using the $CaCl_2$-heat shock method. Both orientations of inserted oligoduplexes are possible, thus colony PCR using standard forward and reverse pJET1 sequencing primers followed by restriction mapping of PCR products with BglII, XbaI and NotI was carried out in order to identify recombinants plasmids which contain inserted oligoduplexes in orientation shown in FIG. 4. Several positives were sequenced to be sure that their structures are correct. Then the plasmid which contains the inserted 3A duplex in correct orientation was named pJET1-3A, while the other one containing the inserted 3B duplex was named pJET1-3B.

Properties of pJET1-3A and pJET1-3B

In order to test if inserted duplexes 3A and 3B preserve functional activity of mutant Eco47I restriction endonuclease, crude cell extracts were prepared from both DH10B [pAC-Eco47IIM+pJET1-3A] and DH10B [pAC-Eco47IIM+pJET1-3B] and incubated with phage % DNA. FIG. 5 shows that the inserted 3A duplex (plasmid pJET1-3A) decreases the activity of Eco47I slightly, while insertion of 3B (plasmid pJET1-3B) results in nearly complete loss of activity. To test if remaining activities of mutant enzymes are enough to destroy unprotected host DNA in vivo and to kill transformed cells, plasmids pJET1-3A and pJET1-3B were used to transform competent cells of DH10B. No colonies carrying pJET1-3A were observed, while small colonies (non-viable in subsequent passage) resulted after the introduction of pJET1-3B into DH10B. Basing on these results we concluded that pJET1-3A kills transformed cells efficiently and therefore may be used as an improved positive selection cloning vector which contains T7 promoter and additional targets of restriction enzymes close to the cloning site.

Preparation of pJET1-3A Vector Suitable for Cloning of Blunt-ended DNA

Recombinant plasmid pJET1-3A is toxic to the host. Thus DNA of this plasmid was isolated from DH10B harbouring an additional plasmid, pAC-Eco47IIM. This plasmid ensures in vivo protection of Eco47I targets and encodes resistance to chloramphenicol. Two alternative approaches, both performing very well, were used to prepare vector DNA which is suitable for cloning of blunt-ended DNA fragments and which is free from contaminating pAC-Eco47IIM.

I. Eco32I-digested vector pJET1-3A DNA was prepared from a mixture of two plasmids (pAC-Eco47IIM+pJET1-3A) by 1 hour cleavage of 1.5 micrograms of plasmid DNA preparation with 10 units of Eco32I in a 150 microliter reaction buffer $R^+$. Then the enzyme was inactivated by heating at 65° C. for 20 minutes, and linearized cloning vector pJET1-3A was separated from supercoiled supplementary plasmid pAC-Eco47IIM by agarose gel electrophoresis followed by purification using DNA Extraction Kit. The concentration of purified DNA was determined spectrophotometrically (ND1000; Nanodrop Technologies, Wilmington, Del.).

II. *Escherichia coli* wild-type strain RFL47 was used to prepare cloning vector by alternative approach. RFL47 is a wild-type producer of Eco47I restriction endonuclease (Janulaitis et al., FEBS Lett., 161 (1983) 213-216), from which Eco47I restriction-modification genes were cloned (Stankevicius et al., Gene 157, (1995) 49-53). In order to test if RFL47 accepts pJET1-3A and supports its replication, RFL47 competent cells were prepared and transformed with the preparation of pJET1.2 using the $CaCl_2$-heat shock method. Transformation mixture was spread onto LB-agar plates supplemented with ampicillin. Plates were incubated overnight at 37° C. On the next morning several individual colonies were picked and streaked on LB-agar-ampicillin and LB-agar-ampicillin-chloramphenicol plates in order to screen for those transformants that received pJET1.2 alone and which are therefore resistant to ampicillin but not to chloramphenicol. A couple of positives were then used to inoculate 5 ml LB medium supplemented with ampicillin, and after overnight growth at 37° C. with shaking plasmid DNAs were isolated from biomasses using GeneJET™ Plasmid Miniprep Kit and used to prepare Eco32I-linearized cloning vector.

Examples described below demonstrate the utility of improved positive selection cloning vector pJET1-3A in cloning experiments and in downstream applications which require the presence of functionally active T7 promoter next to the cloning site.

From the examples described herein, one skilled in the art can easily ascertain the essential principles of this invention and without departing from the spirit and scope thereof, can make various modifications and changes of the invention in adapting to specific uses and conditions.

EXAMPLE 1

Positive Selection Efficiency of Improved Vectors in Cloning of Small Oligoduplexes To determine how well the positive selection system employing modified eco47IR gene would perform in the cloning of short DNA fragments, which are inserted in frame with the toxic gene, the following model experiment was performed. The DNA oligonucleotide ARV (5' ACCGGT 3'), which is self-complementary and contains Cfr10I target, was synthesized. Twenty microliters of annealing mixture were prepared by adding 2 microliters of ARV (100 pmol/µl) to 16 microliters of water and two microliters of 10× ligase buffer. Annealing was carried out in PCR machine (Master-Cycler, Eppendorf) gradually decreasing the annealing mixture temperature (95° C.—5 minutes, 80° C.—2 minutes, 70° C.—2 minutes, 60° C.—2 minutes, 50° C.—2 minutes, 40° C.—2 minutes, 30° C.—2 minutes, 20° C.—2 minutes, 10° C.—2 minutes, 4° C.—2 minutes). Two microlitres of the annealed oligoduplex were then mixed with two microliters of 10× ligase buffer, 50 ng of Eco32I-cleaved pJET1-3A, water (up to 19 microliters) and ligation reaction initiated by adding 1 microliter of T4 DNA ligase (5 units). The ligation reaction was incubated at room temperature for 60 minutes and then 10 microliters of the reaction mixture were used to transform 100 microliters of DH10B competent cells using the $CaCl_2$-heat shock method. Ten colonies out of 150 obtained after the transformation were randomly picked, inoculated in LB-ampicillin broth and next day isolated using the GeneJET™ Plasmid Miniprep Kit. Isolated plasmid DNAs were digested with Cfr10I. The latter contains a single target within pJET1-3A. In case if isolated plasmid contains additional Cfr10I target which appeared during the cloning of ARV duplex, one could expect appearance of two cleavage products with calculated sizes of ~1.45 kb and ~1.72 kb, while in case of pJET1-3A cleavage results in a single fragment of ~3.2 kb. The results of this experiment are presented in FIG. 6. These results show that 9 out of 10 isolated plasmids are recombinant and contain the cloned ARV oligoduplex. Sequencing of two recombinant plasmids demonstrated that their structures are correct, while sequencing of the only clone which was not recombinant (FIG. 6, clone No. 8) revealed one nucleotide deletion at the cloning site in this clone. This damage resulted in a shifted reading frame of eco47IR, leading to its inactivation. All these results show that in-frame insertion of oligoduplex as short as 6 nucleotides and encoding only two amino acid residues into the modified positive selection cloning gene eco47IM (re-cleaved with Eco32I) disrupts functional activity of encoded toxic protein.

EXAMPLE 2

Positive Selection Efficiency of Improved Vectors in Cloning of Medium Size DNA Fragments To test if the improved cloning vector is suitable for cloning of medium size DNA fragments encompassing the full-length genes and for their subsequent inducible in vivo expression, the following model experiment was carried out. The DNA fragment of 1040 bp and containing the gene hphIMA encoding the m6A-specific HphI methyltransferase (Lubys et al., NAR, 1996) was PCR-amplified using PCR primers 1-HA and 2-HA (FIG. 7), while DNA of pET-AMVR-HphIA served as a template. PCR reaction mixture (100 microliters) was prepared by mixing one microliter of pET-AMVRT-HphIA DNA (50 ng/µl) with 1 microliter of 1-HA primer (100 pmol/µl), 1 microliter of 2-HA primer (100 pmol/µl), 10 microliters of 10× High Fidelity PCR Buffer, 10 microliters 2 mM dNTP, 6 microliters 25 mM $MgCl_2$, 70 microliters of water and 1 microliter of High Fidelity Enzyme Mix. PCR was performed using Mastercycler (Eppendorf) using following reaction conditions: initial denaturation, 94° C., 4 minutes; denaturation, 94° C., 1 minute; annealing, 56° C., 1 minute; extension, 72° C., 1.5 minutes. After 30 cycles of amplification the final extension at 72° C. was done (5 minutes). The resulting DNA fragment was separated from free primers and template DNA by agarose gel electrophoresis followed by purification using DNA Extraction Kit. The concentration of purified DNA was determined spectrophotometrically. According to recommendations of manufacturer the High Fidelity Enzyme Mix generates both blunt-ended and 3'-dA tailed PCR products, therefore blunting of amplified DNA fragment prior cloning is recommended. Blunting and cloning of purified DNA fragment was carried out following recommendations of the GeneJET™ PCR Cloning Kit protocol and using components of that kit. The blunting reaction (20 microliters) was set-up by mixing 10 microliters of 2× Reaction Buffer with 0.5 microliters of PCR fragment (~130 ng), 6.7 microliters of water and 1 microliter of Blunting enzyme. The reaction was incubated for 5 minutes at 70° C. in water bath and then placed on ice for 10 seconds. Then 0.8 microliters (50 ng) of Eco32I-cleaved pJET1-3A DNA were added to the reaction and ligation reaction initiated by adding 1 microliter of T4 DNA ligase from the same kit. The reaction was incubated for 5 minutes at 22° C. and then 5 microliters of the ligation reaction were used to transform 100 microliters of DH10B competent cells using the $CaCl_2$-heat shock method. Ten colonies out of several hundred obtained after the transformation were randomly picked, inoculated in LB-ampicillin broth and next day isolated using the GeneJET™ Plasmid Miniprep Kit. Isolated plasmid DNAs were digested with BglII, which contains two targets within pJET1-3A separated one from another by 46 bp. These targets are located on both sides of the Eco32I target used for cloning, thus the cloned DNA fragment can be easily visualized by BglII cleavage followed by electrophoretic analysis of reaction products. The PCR-amplified DNA fragment, which was used in this experiment, has no BglII targets. Thus, in case if the fragment was cloned, one could expect to observe cleavage products with calculated sizes of 3.2 kb and ~1.1 kb. The results of this experiment are presented in FIG. 8. These results show that all 10 isolated plasmids contain cloned DNA fragments, while the size of the cloned fragment is correct in nine of them. To determine the orientation of cloned hphIMA gene, restriction mapping of nine positives was done using EcoRI, which contains one target within the cloned fragment and one target within the cloning vector pJET1-3A. Mapping revealed that expression of hphIMA is under the control of T7 promoter in two plasmids (which were named pJET-HphMIA-1 and pJET-HphMIA-2), while in remaining seven recombinant plasmids orientation of hphIMA is opposite. All these results show that the improved vector pJET1-3A is suitable for positive selection of medium-sized DNA fragments.

EXAMPLE 3

Performance of T7 Promoter Carried by pJET1-3A In Vivo

Very often cloning experiments are followed by inducible expression of cloned genes. In order to demonstrate that the T7 promoter, inserted into the improved cloning vector pJET1-3A, is functional and may be used for inducible protein synthesis, expression experiment was carried out using recombinant plasmids pJET-HphMIA-1 and pJET-HphMIA-2 described above. It is well known that the inducible T7 expression system is composed of two main components—T7 promoter, from which high level transcription of target gene is accomplished by T7 RNA polymerase, and the T7 RNA polymerase itself (Studier, F. W., Moffatt, B. A, J. Mol. Biol., 1986, 189:113-130). Two general strategies may be used to provide active T7 RNA polymerase to the cell: (i) infection by a phage carrying the inserted gene for T7 RNA polymerase, or (ii) induction of chromosomally located T7 RNA polymerase gene under control of the lac promoter. The first approach is superior for toxic proteins, while the second one is suitable for large range of non-toxic proteins (Studier, F. W., Moffatt, B. A, J. Mol. Biol., 1986, 189:113-130). HphI m6A-specific methyltransferase is not toxic to *E. coli* cells (Lubys, 1996, NAR), thus the second way was employed for T7 promoter validation purposes. ER2566 strain contains a chromosomal copy of the T7 RNA polymerase gene under control of lac promoter which can be induced by IPTG. ER2566 cells were transformed with plasmids pJET-HphMIA-1 and pJET-HphMIA-2 using the $CaCl_2$-heat shock method. One ampicillin-resistant colony from each transformation was used to inoculate 5 ml LB-ampicillin broth which was then grown overnight with shaking at 37° C. In the next morning 400 microliters of each culture were used to inoculate 20 ml of fresh LB broth supplemented with ampicillin. Seeded cultures were incubated at 37° C. with shaking (250 rpm) until their optical densities at 600 nm reached 0.5-0.6 optical units. At that point 1 ml sample from each culture was removed, while remaining cultures were induced by addition of IPTG to the final concentration of 1 mM and their growth was continued for 3 hours at 37° C. with shaking. After that aliquots of 500 microliters were taken from induced cultures. Then uninduced and induced cells were sedimented by centrifugation and resuspended in 37.5 microliters of water and 10 microliters of 5× Loading Buffer. After addition of 2.5 microliters of 20× Reducing Agent samples were incubated for 10 minutes at 100° C. and then 4 microliters of each sample were loaded onto the 8% SDS-polyacrylamide gel. Eight microliters of PageRuler™ Prestained Protein Ladder were also loaded to monitor protein separation during SDS-polyacrylamide gel electrophoresis and for approximate sizing of proteins. Results of this experiment (FIG. 9) indicate the appearance of the same single sharp protein band in both induced cultures. The approximate size of this protein (38-39 kDa) coincides very well with that calculated for m6A-specific HphI methyltransferase (39.7 kDa). This experiment demonstrates that the T7 promoter located within the improved positive selection cloning vector pJET1-3A is functional in vivo and may be used for inducible protein synthesis.

EXAMPLE 4

Performance of T7 Promoter Carried by pJET1-3A In Vitro

In vitro transcription of cloned DNA fragments is another application, which very often follows the cloning step. There are a lot of in vitro transcription kits provided by multiple companies which are based on the use of T7 RNA polymerase which transcribes from T7 promoter located upstream the DNA fragment of interest. To demonstrate that the T7 promoter, inserted into the improved cloning vector pJET1-3A, is operational and may be used for in vitro synthesis of RNA, the following model experiment was carried out. DNA of plasmid pJET-HphMIA-1 (described above) was cleaved in parallel with restriction endonucleases BseJI, NcoI and XbaI. All these enzymes contain single cleavage sites within the cloned hphIMA gene and are distanced from the T7 promoter by 842, 1092 and 1123 nucleotides, respectively. After completion of cleavage reaction the reaction mixtures were extracted with phenol/chloroform, twice with chloroform and then DNA precipitated with 2 volumes of ethanol in presence of NaCl at final concentration of 0.2M. Precipitated DNAs were washed with 75% ethanol, air dried and then dissolved in DEPC treated water. In vitro transcription was performed using T7 Transcription Kit following recommendations of manufacturer. Four transcription reaction mixtures (volume of each reaction—50 microliters) were prepared. Three of them contained DNA of pJET-HphMIA-1 linearized with BseJI, NcoI or XbaI, while the fourth contained the control DNA from the kit. All four reaction mixtures were divided into two equal parts, and then one sample from each reaction was incubated for 2 hours at 37° C., while the other one—at 0° C. All reactions were then stopped by cooling at −20° C. After mixing of 5 microliters of reaction mixtures with 2 microliters of 5× Loading Dye Solution (15% ficoll, 100 mM EDTA, pH8.0, 0.5% SDS) and 3 microliters of water prepared samples were incubated for 10 minutes at 70° C., cooled in ice and then loaded onto the 1.5% agarose gel using TAE electrophoresis buffer supplemented with ethidium bromide (final concentration 0.5 micrograms per milliliter). Results of this experiment (FIG. 10) indicate the appearance of synthesized RNA in all samples incubated at 37° C., while the yield of produced RNA in control reaction is comparable with that obtained in reactions where DNA of pJET1-3A was used. This experiment demonstrates that the T7 promoter in pJET1-3A is functional in vitro and may be used for in vitro synthesis of RNA employing purified T7 RNA polymerase.

The invention claimed is:

1. A positive selection vector for transformation into a host cell comprising a toxic gene encoding a product that is lethal to the host cell, wherein the toxic gene comprises:
   an essential sequence region whose integrity is necessary in order for the encoded toxic gene product to be lethal to the host cell;
   an inessential sequence region which encodes a section of the toxic product and whose integrity is not essential in order for the encoded toxic gene product to be lethal to the host cell;
   a regulatory sequence inserted in-frame into the inessential sequence region and encoding amino acids additional to the encoded toxic gene product; and
   a cloning site within the essential sequence region for insertion of a nucleic acid sequence,
   wherein the regulatory sequence and the cloning site are positioned so as to allow the regulatory sequence to be operably linked to a nucleic acid sequence when the nucleic acid sequence is inserted into the cloning site and wherein the toxic gene encodes a nuclease.

2. A vector according to claim 1 wherein the toxic gene is eco47IR.

3. A vector according to claim 1 wherein the regulatory sequence is a T7 promoter sequence.

4. A vector according to claim 1 wherein the toxic gene is eco47IR, the regulatory sequence is a T7 promoter sequence, the cloning site is an Eco32I site and the vector further comprises a replication region and an ampicillin resistance gene.

5. A vector according to claim 1 further comprising a nucleic acid molecule inserted into the toxic gene at the cloning site.

6. A recombinant host cell comprising the vector of claim 1.

7. A kit for cloning of a nucleic acid molecule, comprising the vector of claim 1.

8. A method for producing a positive selection vector of claim 1 comprising the steps of:
   a) selecting a vector comprising a toxic gene encoding a product that is lethal to the host cell; and
   b) inserting a regulatory sequence into the sequence of the toxic gene at an inessential region of the toxic gene which encodes a section of the toxic product and whose integrity is not essential in order for the encoded toxic gene product to be lethal to the host cell;
   wherein the sequence of the toxic gene further comprises a cloning site at a region within the sequence of the toxic gene whose integrity is essential in order for the product encoded by the toxic gene to be lethal to the host cell and wherein the toxic gene encodes a nuclease.

9. A method according to claim 8, further comprising the step of introducing the cloning site into the toxic gene sequence by site-specific mutagenesis.

10. A method of cloning a nucleic acid molecule comprising the steps of:
    a) cutting a positive selection vector according to claim 1 at the cloning site to create a linearized vector; and
    b) ligating the nucleic acid molecule into the linearized vector to form a circularised vector product.

11. A method of expressing a nucleic acid molecule comprising transforming the vector of claim 5 into a host cell, and culturing the cell under conditions suitable for expression of the nucleic acid molecule.

12. A positive selection vector for transformation into a host cell comprising a toxic gene encoding a product that is lethal to the host cell, wherein the toxic gene comprises:
    an essential sequence region whose integrity is necessary in order for the encoded toxic gene product to be lethal to the host cell;

an inessential sequence region which encodes a section of the toxic product and whose integrity is not essential in order for the encoded toxic gene product to be lethal to the host cell;
a promoter sequence inserted in-frame into the inessential sequence region; and
a cloning site within the essential sequence region for insertion of a nucleic acid sequence,
wherein the promoter sequence and the cloning site are positioned so as to allow the promoter sequence to be operably linked to a nucleic acid sequence when the nucleic acid sequence is inserted into the cloning site,
wherein the toxic gene is eco47IR,
and wherein the promoter sequence comprises a T7, SP6, T3, phage lambda PL, phage lambda PR, Plac type, or a ParaBAD promoter.

* * * * *

SEQUENCE LISTING

<160> NUMBER OF SEQ ID NOS: 11

<210> SEQ ID NO 1
<211> LENGTH: 55
<212> TYPE: DNA
<213> ORGANISM: Artificial Sequence
<220> FEATURE:
<223> OTHER INFORMATION: part of synthetic Mu transposon Tn-Km-Mre

<400> SEQUENCE: 1
agatctgcgc cggcgcacga aaaacgcgaa agcgtttcac gataaatgcg aaaac     55

```
<210> SEQ ID NO 2
<211> LENGTH: 15
<212> TYPE: DNA
<213> ORGANISM: Escherichia coli

<400> SEQUENCE: 2
aagaatgctg aggaa                                                      15

<210> SEQ ID NO 3
<211> LENGTH: 30
<212> TYPE: DNA
<213> ORGANISM: Escherichia coli

<400> SEQUENCE: 3
gatgaagtat catctaagaa tttaaatgaa                                       30

<210> SEQ ID NO 4
<211> LENGTH: 45
<212> TYPE: DNA
<213> ORGANISM: Artificial Sequence
<220> FEATURE:
<223> OTHER INFORMATION: 3Adir oligonucleotide

<400> SEQUENCE: 4
ccggaagatc tggcggccgc tctccctata gtgagtcgta ttacg                      45

<210> SEQ ID NO 5
<211> LENGTH: 45
<212> TYPE: DNA
<213> ORGANISM: Artificial Sequence
<220> FEATURE:
<223> OTHER INFORMATION: 3Arev oligonucleotide

<400> SEQUENCE: 5
ccggcgtaat acgactcact atagggagag cggccgccag atctt                      45

<210> SEQ ID NO 6
<211> LENGTH: 45
<212> TYPE: DNA
<213> ORGANISM: Artificial Sequence
<220> FEATURE:
<223> OTHER INFORMATION: 3Bdir oligonucleotide

<400> SEQUENCE: 6
ccggaggaga tctgcggccg cgtctcccta tagtgagtcg tatta                      45

<210> SEQ ID NO 7
<211> LENGTH: 45
<212> TYPE: DNA
<213> ORGANISM: Artificial Sequence
<220> FEATURE:
<223> OTHER INFORMATION: 3Brev oligonucleotide

<400> SEQUENCE: 7
ccggtaatac gactcactat agggagacgc ggccgcagat ctcct                      45

<210> SEQ ID NO 8
<211> LENGTH: 46
<212> TYPE: DNA
<213> ORGANISM: Artificial Sequence
<220> FEATURE:
<223> OTHER INFORMATION: 1-HA primer for HphIMA methyltransferase

<400> SEQUENCE: 8
actagtaagg agataagaat gctgaataat cctaaatacc ctaaag                     46
```

```
<210> SEQ ID NO 9
<211> LENGTH: 31
<212> TYPE: DNA
<213> ORGANISM: Artificial Sequence
<220> FEATURE:
<223> OTHER INFORMATION: 2-HA primer for HphIMA methyltransferase

<400> SEQUENCE: 9
gcggccgctt atctattttc cactaaaaac a                              31

<210> SEQ ID NO 10
<211> LENGTH: 5
<212> TYPE: PRT
<213> ORGANISM: Escherichia coli

<400> SEQUENCE: 10

Lys Asn Ala Glu Glu
1               5

<210> SEQ ID NO 11
<211> LENGTH: 10
<212> TYPE: PRT
<213> ORGANISM: Escherichia coli

<400> SEQUENCE: 11

Asp Glu Val Ser Ser Lys Asn Leu Asn Glu
1               5                   10
```